US008619256B1

(12) United States Patent
Pelletier et al.

(10) Patent No.: US 8,619,256 B1
(45) Date of Patent: Dec. 31, 2013

(54) SYSTEMS AND METHODS FOR MONITORING THE PROPERTIES OF A FLUID CEMENT COMPOSITION IN A FLOW PATH (75) Inventors: Michael T. Pelletier, Houston, TX (US); Christopher Michael Jones, Houston, TX (US); B. Raghava Reddy, Houston, TX (US); Ashok Santra, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 13/615,696

(22) Filed: Sep. 14, 2012

(51) Int. Cl.
*G01N 15/02* (2006.01)

(52) U.S. Cl.
USPC .......................................... 356/335; 356/336

(58) Field of Classification Search
USPC ................... 356/335–343; 367/35, 105, 31; 166/250.03, 250.01, 285, 305.1, 66
See application file for complete search history.

(56) References Cited

U.S. PATENT DOCUMENTS

| 4,003,431 | A | * | 1/1977 | Novotny et al. ............... 166/293 |
| 4,618,939 | A | | 10/1986 | Davis |
| 5,027,267 | A | | 6/1991 | Pitts et al. |
| 5,400,137 | A | | 3/1995 | Winslow et al. |
| 5,418,614 | A | | 5/1995 | Brost et al. |
| 5,489,977 | A | | 2/1996 | Winslow et al. |
| 5,775,803 | A | * | 7/1998 | Montgomery et al. ............ 366/2 |
| 6,018,496 | A | * | 1/2000 | Stanke et al. ................... 367/35 |
| 6,042,259 | A | * | 3/2000 | Hines et al. ..................... 366/17 |
| 6,198,531 | B1 | | 3/2001 | Myrick et al. |
| 6,529,276 | B1 | | 3/2003 | Myrick |
| 7,123,844 | B2 | | 10/2006 | Myrick |
| 7,138,156 | B1 | | 11/2006 | Myrick et al. |
| 7,149,146 | B2 | * | 12/2006 | Kuijk et al. ...................... 367/35 |
| 7,472,748 | B2 | | 1/2009 | Gdanski et al. |
| 7,623,233 | B2 | | 11/2009 | Freese et al. |
| 7,697,141 | B2 | | 4/2010 | Jones et al. |
| 7,712,527 | B2 | | 5/2010 | Roddy |
| 7,834,999 | B2 | | 11/2010 | Myrick et al. |
| 7,911,605 | B2 | | 3/2011 | Myrick et al. |
| 7,920,258 | B2 | | 4/2011 | Myrick et al. |
| 7,938,175 | B2 | | 5/2011 | Skinner et al. |
| 7,963,323 | B2 | * | 6/2011 | Bailey ....................... 166/250.03 |

(Continued)

OTHER PUBLICATIONS

Brost et al., "Optical Methods for Monitoring Treating Chemicals in Oilfield Water Systems," SPE 22781, 217-232, 1991.

(Continued)

*Primary Examiner* — Sang Nguyen
(74) *Attorney, Agent, or Firm* — John W. Wustenberg; McDermott Will & Emery LLP (57) ABSTRACT

Optical analysis systems may be useful in systems and methods for various properties of fluid cement compositions. For example, a method may include generating with an optical computing device a plurality of output signals corresponding to a plurality of time points and a characteristic of a fluid cement composition at a monitoring location within a flow path, the optical computing device having an electromagnetic radiation source configured to optically interact with the fluid cement composition and an integrated computational element, wherein the integrated computational element is configured to produce and convey optically interacted light to a detector which generates a plurality of output signals corresponding to the characteristic at a plurality of time points; receiving the plurality of output signals with a signal processor communicably coupled to the detector; and determining a difference between at least two of the output signals with the signal processor.

20 Claims, 3 Drawing Sheets

(56) References Cited

U.S. PATENT DOCUMENTS

| | | |
|---|---|---|
| 8,049,881 B2 | 11/2011 | Myrick et al. |
| 8,141,633 B2 | 3/2012 | Hampton et al. |
| 2007/0282647 A1 | 12/2007 | Freese et al. |
| 2008/0231849 A1 | 9/2008 | Myrick et al. |
| 2008/0276687 A1 | 11/2008 | Myrick et al. |
| 2009/0073433 A1 | 3/2009 | Myrick et al. |
| 2009/0097024 A1 | 4/2009 | Blackburn et al. |
| 2009/0118866 A1* | 5/2009 | Dykstra et al. ............... 700/265 |
| 2009/0140144 A1 | 6/2009 | Myrick et al. |
| 2009/0182693 A1 | 7/2009 | Fulton et al. |
| 2009/0216504 A1 | 8/2009 | Priore et al. |
| 2009/0219512 A1 | 9/2009 | Myrick et al. |
| 2009/0219538 A1 | 9/2009 | Myrick et al. |
| 2009/0219539 A1 | 9/2009 | Myrick et al. |
| 2009/0250613 A1 | 10/2009 | Myrick et al. |
| 2009/0299946 A1 | 12/2009 | Myrick et al. |
| 2009/0316150 A1 | 12/2009 | Myrick et al. |
| 2010/0050905 A1 | 3/2010 | Lewis et al. |
| 2010/0051266 A1 | 3/2010 | Roddy et al. |
| 2010/0051275 A1 | 3/2010 | Lewis et al. |
| 2010/0073666 A1 | 3/2010 | Perkins et al. |
| 2010/0101319 A1* | 4/2010 | Ramakrishan et al. .... 73/152.51 |
| 2010/0141952 A1 | 6/2010 | Myrick et al. |
| 2010/0149537 A1 | 6/2010 | Myrick et al. |
| 2010/0153048 A1 | 6/2010 | Myrick et al. |
| 2010/0182600 A1 | 7/2010 | Freese et al. |
| 2010/0195105 A1 | 8/2010 | Myrick et al. |
| 2010/0245096 A1 | 9/2010 | Jones et al. |
| 2010/0265509 A1 | 10/2010 | Jones et al. |
| 2010/0302539 A1 | 12/2010 | Myrick et al. |
| 2010/0305741 A1 | 12/2010 | Myrick |
| 2010/0328669 A1 | 12/2010 | Myrick et al. |
| 2011/0048715 A1* | 3/2011 | Lewis et al. .................. 166/293 |
| 2011/0199610 A1 | 8/2011 | Myrick et al. |
| 2011/0308788 A1 | 12/2011 | Ravi et al. |
| 2012/0205103 A1 | 8/2012 | Ravi et al. |

OTHER PUBLICATIONS

Myrick, et al. "Spectral Tolerance Determination for Multivariate Optical Element Design," Fresenuis' Journal of Analytical Chemistry, 369:2001; pp. 351-355.

Ramachandran, et al., "Chemical Kinetics in Real Time: Using the Differential Rate Law and Discovering the Reaction Orders," A Physical Chemistry Laboratory Experiment, Journal of Chemical Education; 1996, pp. 686-689.

\* cited by examiner

SYSTEMS AND METHODS FOR MONITORING THE PROPERTIES OF A FLUID CEMENT COMPOSITION IN A FLOW PATH

BACKGROUND

The present invention relates to optical analysis systems and methods for analyzing fluids and, in particular, to systems and methods for analyzing the properties of a fluid cement composition.

Fluid cement compositions like dry cement blends and cement slurries can be complex fluid systems where variations from a precise formulation can result in a plurality of detrimental outcomes including, but not limited to, (1) failing to provide zonal isolation, thereby allowing undesirable fluids to enter the wellbore, which in severe instances may yield well blowouts, (2) exceeding fracture pressures, thereby causing wellbore and formation damage, (3) producing an unpredictable setting time, which may result in premature setting in an undesired location or excessive setting times that delay subsequent operations, and/or (4) causing inhomogeneous setting reactions, which can result in reduced mechanical integrity of the set cement composition. Remediating the various detrimental outcomes can prove to be costly and time consuming, and in some severe cases have significant environmental impact.

Variations in the precise formulation of an otherwise properly designed fluid cement composition (i.e., having all the request components in the proper amounts) can arise from, inter alia, compositional inhomogeneity throughout the fluid cement composition. Most often compositional inhomogeneity arises from particulate segregation and variations in cement-to-water ratios. For example, dry cement blends often include cement particles and filler particles of various sizes and specific gravities and, in some instances, chemicals in a fine powder form. Long-term storage and transportation of such a dry cement blend can cause the particles to separate based on, inter alia, density, size, and shape. To mitigate inhomogeneity in dry cement blends, an extensive mixing process of small batches of dry cement blend are performed. In many instances the mixing processes are in excess of what is needed, which consumes time and energy, thereby driving up costs.

In cement slurries, for example, density variations in the cement slurry can be a common problem in addition to compositional inhomogeneity described above. Density variations lead to unpredictable setting times. Further, density variation can cause a mismatch between the slurry and the pressure of the formation, which can lead to formation fluids entering the wellbore or slurry loss into the formation.

Monitoring the homogeneity and/or setting status of cement fluid compositions may enable the mitigation of the detrimental outcomes and costly remedial operations associated therewith. However, in relation to wellbore operations, such monitoring should be remote and robust to the chemicals and temperatures found in a subterranean formation. Well logging operations, which can add significant nonproductive time and cost to a cementing operation, are the primary avenue to downhole analysis.

Accordingly, in situ monitoring of cement fluid compositions may not only provide higher quality control in cementing operations but may also reduce the cost and mitigate the need for remedial operations.

SUMMARY OF THE INVENTION

The present invention relates to optical analysis systems and methods for analyzing fluids and, in particular, to systems and methods for analyzing the properties of a fluid cement composition.

One embodiment of the present invention may include a method that comprises containing within a flow path a dry cement blend; optically interacting the dry cement blend with an integrated computational element at a plurality of time points, thereby generating a plurality of output signals corresponding to a characteristic of the dry cement blend at the plurality of time points; receiving the plurality of output signals with a signal processor; and determining a difference between at least two output signals of the plurality of output signals with the signal processor.

Anther embodiment of the present invention may include a method that comprises containing within a flow path a fluid that comprises a cement particle, the flow path providing at least a first monitoring location and a second monitoring location; optically interacting the fluid at the first monitoring location with a first integrated computational element, thereby generating a first output signal corresponding to a characteristic of the fluid; optically interacting the fluid at the second monitoring location with a second integrated computational element, thereby generating a second output signal corresponding to the characteristic of the fluid; receiving the first output signal and the second output signal with a signal processor; and determining a difference between the first output signal and the second output signal with the signal processor.

Yet another embodiment of the present invention may include a system that comprises a flow path containing a dry cement blend; and at least two optical computing devices arranged in the flow path for monitoring the dry cement blend, each of the at least two optical computing devices independently having at least one integrated computational element configured to optically interact with the dry cement blend and thereby generate optically interacted light, and at least one detector arranged to receive the optically interacted light and generate an output signal corresponding to a characteristic of the dry cement blend.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present invention relates to optical analysis systems and methods for analyzing fluids and, in particular, to systems and methods for analyzing the properties of a fluid cement composition.

The exemplary systems and methods described herein employ various configurations of optical computing devices, also commonly referred to as "opticoanalytical devices," for the real-time or near real-time monitoring of fluids. The disclosed systems and methods may be suitable for use in the oil and gas industry since the described optical computing devices provide a cost-effective, rugged, and accurate means for monitoring hydrocarbon quality in order to facilitate the efficient management of oil/gas production. It will be appreciated, however, that the various disclosed systems and methods are equally applicable to other technology fields including, but not limited to, the food and drug industry, industrial applications, mining industries, or any field where it may be advantageous to determine in real-time or near real-time a characteristic of a specific substance in a flowing fluid, especially to determine the quality of the substance.

The optical computing devices disclosed herein, which are described in more detail below, can advantageously provide real-time or near real-time monitoring of a fluid that cannot presently be achieved with either onsite analyses at a job site or via more detailed analyses that take place in a laboratory. A significant and distinct advantage of these devices is that they can be configured to specifically detect and/or measure a particular characteristic of interest of a material of interest (e.g., a fluid), thereby allowing qualitative and/or quantitative analyses of the material of interest to occur without having to undertake a time-consuming sample processing procedure. With real-time or near real-time analyses on hand, the exemplary systems and methods described herein may be able to provide some measure of proactive or responsive control over the quality of the material of interest, enable the collection and archival of information relating to the material of interest in conjunction with operational information to optimize subsequent operations, and/or enhance the capacity for remote job execution.

The optical computing devices suitable for use in the present embodiments can be deployed at two or more fluidly communicable points within a flow path to monitor the fluid and the compositional differences of the fluid that may be present between the two or more points. In some cases, for example, the optical computing devices can be used to monitor changes to a fluid that take place over time (e.g., at a plurality of time points) or over a predetermined distance in the flow path. In some cases, the optical computing devices can be used to monitor changes to the fluid as a result of adding an analyte thereto, removing an analyte therefrom, or exposing the fluid to a condition that potentially changes a characteristic of the fluid in some way (e.g., increasing temperature or mixing). Thus, the systems and methods described herein may be configured to monitor the properties of fluids and, more particularly, to monitor any changes thereto, which may translate to quality control analysis of the fluid and/or the treatment operation in which the fluid is being used. In at least one aspect, this may prove advantageous in determining the proper timing for the various stages of a cementing operation.

As used herein, the term "fluid" refers to any substance that is capable of flowing, including particulate solids, liquids, gases, slurries, emulsions, powders, muds, glasses, combinations thereof, and the like. In some embodiments, the fluid can be an aqueous fluid, including water or the like. In some embodiments, the fluid can be a non-aqueous fluid, including organic compounds, more specifically, hydrocarbons, oil, a refined component of oil, petrochemical products, and the like. In some embodiments, the fluid can be a treatment fluid (e.g., a spacer fluid, a cement fluid composition, a drilling fluid, and the like) or a formation fluid as found in the oil and gas industry. Fluids can include various flowable mixtures of solids, liquids, and/or gases. Illustrative gases that can be considered fluids according to the present embodiments include, for example, air, nitrogen, carbon dioxide, hydrogen sulfide ($H_2S$), argon, helium, methane, ethane, butane, and other hydrocarbon gases, combinations thereof and/or the like.

As used herein, the term "cement fluid composition" refers to any fluid that comprises a cement. Cement is not necessarily hydraulic cement, since other types of materials (e.g., polymers like epoxies and latexes) can be used in place of, or in addition to, a hydraulic cement. Examples of cements may include, but are not limited to, hydraulic cements, Portland cement, gypsum cements, calcium phosphate cements, high alumina content cements, silica cements, high alkalinity cements, shale cements, acid/base cements, magnesia cements (e.g., Sorel cements), fly ash cements, zeolite cement systems, cement kiln dust cement systems, slag cements, micro-fine cements, epoxies, bentonites, latexes, and the like, any derivative thereof, and any combination thereof. Cement fluid compositions may be cement slurries that include water or dry cement blends. Unless otherwise specified, the term "fluid" encompasses cement fluid compositions, the term "cement fluid compositions" encompasses cement slurries and dry cement blends, and the term "cement slurry" encompasses foamed cements. As used herein, the term "dry cement blend" refers to a mixture of solid particles including at least some cement particles and is not hydrated beyond about ambient conditions (e.g., no additional water has been added).

As used herein, the term "chemical reaction process" or "chemical reaction" refers to a process that leads to the transformation of one set of chemical substances to another. As known to those skilled in the art, chemical reactions involve one or more reagents, as described below, that chemically react either spontaneously, requiring no input of energy, or non-spontaneously typically following the input of some type of energy, such as heat, light, or electricity. The chemical reaction process yields one or more products, which may or may not have properties different from the reagents.

As used herein, the term "characteristic" refers to a chemical, mechanical, or physical property (quantitative or qualitative) of a material of interest (e.g., a dry cement blend, a cement slurry, or analyte thereof). As used herein, the term "analyte" refers to a chemical component. The term analyte encompasses chemical components that are at least one of: present in the material of interest, may be added to the material of interest, involved in a chemical reaction (e.g., reagents and products) transpiring within the material of interest, and not involved in a chemical reaction transpiring within the material of interest. Illustrative characteristics of a material of interest that can be monitored with the optical computing devices disclosed herein can include, for example, chemical composition (e.g., identity and concentration in total or of individual analytes), impurity content, pH, viscosity, density, ionic strength, total dissolved solids, salt content, porosity, opacity, bacteria content, particle size distribution, color, temperature, hydration level, oxidation state, and the like. Moreover, the phrase "characteristic of interest" may be used herein to refer to a characteristic of a material of interest.

Exemplary analytes may include, but are not limited to, water, salts, minerals (wollastonite, metakaolin, and pumice), cements (Portland cement, gypsum cements, calcium phosphate cements, high alumina content cements, silica cements, and high alkalinity cements), fillers (e.g., fly ash, fume silica, hydrated lime, pozzolanic materials, sand, barite, calcium carbonate, ground marble, iron oxide, manganese oxide, glass bead, crushed glass, crushed drill cutting, ground vehicle tire, crushed rock, ground asphalt, crushed concrete, crushed cement, ilmenite, hematite, silica flour, fume silica, fly ash, elastomers, polymers, diatomaceous earth, a highly swellable clay mineral, nitrogen, air, fibers, natural rubber, acrylate butadiene rubber, polyacrylate rubber, isoprene rubber, chloroprene rubber, butyl rubber, brominated butyl rubber, chlorinated butyl rubber, chlorinated polyethylene, neoprene rubber, styrene butadiene copolymer rubber, sulphonated polyethylene, ethylene acrylate rubber, epichlorohydrin ethylene oxide copolymer, ethylene propylene rubber, ethylene propylene diene terpolymer rubber, ethylene vinyl acetate copolymer, fluorosilicone rubber, silicone rubber, poly-2,2,1-bicycloheptene (polynorborneane), alkylstyrene, crosslinked substituted vinyl acrylate copolymer, nitrile rubber (butadiene acrylonitrile copolymer), hydrogenated nitrile rubber, fluoro rubber, perfluoro rubber, tetrafluoroethylene/propylene, starch polyacrylate acid graft copolymer, polyvinyl alcohol cyclic acid anhydride graft copolymer, isobutylene maleic anhydride, acrylic acid type polymer, vinylacetate-acrylate copolymer, polyethylene oxide polymer, carboxymethyl cellulose polymer, starch-polyacrylonitrile graft copolymer, polymethacrylate, polyacrylamide, and non-soluble acrylic polymer), hydrocarbons, acids, acid-generating compounds, bases, base-generating compounds, biocides, surfactants, scale inhibitors, corrosion inhibitors, gelling agents, crosslinking agents, anti-sludging agents, foaming agents, defoaming agents, antifoam agents, emulsifying agents, de-emulsifying agents, iron control agents, proppants or other particulates, gravel, particulate diverters, salts, cement slurry loss control additives, gas migration control additives, gases, air, nitrogen, carbon dioxide, hydrogen sulfide ($H_2S$), argon, helium, hydrocarbon gases, methane, ethane, butane, catalysts, clay control agents, chelating agents, corrosion inhibitors, dispersants, flocculants, scavengers (e.g., $H_2S$ scavengers, $CO_2$ scavengers, or $O_2$ scavengers), lubricants, breakers, delayed release breakers, friction reducers, bridging agents, viscosifiers, weighting agents, solubilizers, rheology control agents, viscosity modifiers, pH control agents (e.g., buffers), hydrate inhibitors, relative permeability modifiers, diverting agents, consolidating agents, fibrous materials, bactericides, tracers, probes, nanoparticles, paraffin waxes, asphaltenes, foams, sand or other solid particles, and the like. Combinations of these components can be used as well.

As used herein, the term "flow path" refers to a route through which a fluid is capable of being transported between two points. In some cases, the flow path need not be continuous or otherwise contiguous between the two points. Exemplary flow paths include, but are not limited to, a slurry tank, a flowline, a pipeline, a conduit, a wellbore annulus (e.g., an annulus between a casing and a wellbore or an annulus between a screen and a wellbore), a casing, a liner, a liner string, a hose, a mixer, a pump, a process facility, a storage vessel, a tanker, a railway tank car, a transport barge or ship, a separator, a contactor, a process vessel, and the like, any hybrid thereof, and any combination thereof. In cases where the flow path is a pipeline, or the like, the pipeline may be a pre-commissioned pipeline or an operational pipeline. It should be noted that the term "flow path" does not necessarily imply that a fluid is flowing therein, rather that a fluid is capable of being transported or otherwise flowable therethrough. In some embodiments, a flow path may be a component of a more complex system, for example, skids, trucks, pumps, and the like. In some embodiments, a flow path may comprise more than one section that is separated, but still fluidly communicable, by apparatuses like valves, flow meters, and the like.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation from a substance or sample of the substance, and produce an output of electromagnetic radiation from a processing element arranged within the optical computing device. The processing element may be, for example, an integrated computational element (ICE) used in the optical computing device. As discussed in greater detail below, the electromagnetic radiation that optically interacts with the processing element is changed so as to be readable by a detector, such that an output of the detector can be correlated to at least one characteristic of the substance being measured or monitored. The output of electromagnetic radiation from the processing element can be reflected electromagnetic radiation, transmitted electromagnetic radiation, and/or dispersed electromagnetic radiation. Whether reflected or transmitted electromagnetic radiation is analyzed by the detector may be dictated by the structural parameters of the optical computing device as well as other considerations known to those skilled in the art. In addition, emission and/or scattering by the substance, for example via fluorescence, luminescence, Raman scattering, and/or Raleigh scattering, can also be monitored by the optical computing devices.

As used herein, the term "optically interact" or variations thereof refers to the reflection, transmission, scattering, diffraction, or absorption of electromagnetic radiation either on, through, or from one or more processing elements (i.e., integrated computational elements). Accordingly, optically interacted light refers to electromagnetic radiation that has been reflected, transmitted, scattered, diffracted, or absorbed by, emitted, or re-radiated, for example, using the integrated computational elements, but may also apply to interaction with a fluid or a substance in the fluid.

The exemplary systems and methods described herein will include at least one optical computing device arranged along or in a flow path in order to monitor a characteristic of a material of interest flowing or otherwise contained within the flow path and calculate changes in the characteristic of interest. The exemplary systems and methods described herein may, in some embodiments, include at least two optical computing devices strategically arranged along a flow path in order to monitor a characteristic of a material of interest flowing or otherwise contained therein and calculate differences between the characteristic of interest at the various measurement or monitoring locations (e.g., within and/or outside a wellbore). An optical computing device may include an electromagnetic radiation source, at least one processing element (e.g., integrated computational elements), and at least one detector arranged to receive optically interacted light from the at least one processing element. As disclosed below, however, in at least one embodiment, the electromagnetic radiation source may be omitted and instead the electromagnetic radiation may be derived from the material of interest itself. For example, in some embodiments, a tracer may be incorporated into a cement fluid and/or dry cement blend that is a dye with a strong chromophore or charge-transfer group that would allow for the electromagnetic radiation to be derived from an analyte (i.e., the tracer) in the cement fluid and/or dry cement blend. In some embodiments, the exemplary optical computing devices may be specifically configured for detecting, analyzing, and quantitatively measuring a particular characteristic of the material of interest in the flow path. In other embodiments, the optical computing devices may be general purpose optical devices, with post-acquisition processing (e.g., through computer means) being used to specifically detect the characteristic of interest.

In some embodiments, suitable structural components for the exemplary optical computing devices are described in commonly owned U.S. Pat. No. 6,198,531 entitled "Optical Computational System;" U.S. Pat. No. 6,529,276 entitled "Optical Computational System;" U.S. Pat. No. 7,123,844 entitled "Optical Computational System;" U.S. Pat. No. 7,834,999 entitled "Optical Analysis System and Optical Train;" U.S. Pat. No. 7,911,605 entitled "Multivariate Optical Elements for Optical Analysis System;" U.S. Pat. No. 7,920,258 entitled "Optical Analysis System and Elements to Isolate Spectral Region;" and U.S. Pat. No. 8,049,881 entitled "Optical Analysis System and Methods for Operating Multivariate Optical Elements in a Normal Incidence Orientation;" each of which is incorporated herein by reference in its entirety, and U.S. patent application Ser. No. 12/094,460 entitled "Methods of High-Speed Monitoring Based on the Use of Multivariate Optical Elements;" Ser. No. 12/094,465 entitled "Optical Analysis System for Dynamic Real-Time Detection and Measurement;" and Ser. No. 13/456,467 entitled "Imaging Systems for Optical Computing Devices;" each of which is also incorporated herein by reference in its entirety. As will be appreciated, variations of the structural components of the optical computing devices described in the above-referenced patents and patent applications may be suitable, without departing from the scope of the disclosure, and therefore, should not be considered limiting to the various embodiments or uses disclosed herein.

The optical computing devices described in the foregoing patents and patent applications combine the advantage of the power, precision, and accuracy associated with laboratory spectrometers, while being extremely rugged and suitable for field use. Furthermore, the optical computing devices can perform calculations (analyses) in real-time or near real-time without the need for time-consuming sample processing. In this regard, the optical computing devices can be specifically configured to detect and analyze particular characteristics of interest. As a result, interfering signals are discriminated from those of interest by appropriate configuration of the optical computing devices, such that the optical computing devices provide a rapid response regarding the characteristic of interest as based on the detected output. In some embodiments, the detected output can be converted into a voltage that is distinctive of the magnitude of the characteristic of interest. The foregoing advantages and others make the optical computing devices particularly well suited for field and downhole use.

The optical computing devices can be configured to detect not only the composition and concentrations of an analyte in a material of interest, but they also can be configured to determine physical properties and other characteristics of the material of interest as well, based on their analysis of the electromagnetic radiation received from the substance. For example, the optical computing devices can be configured to determine the concentration of an analyte and correlate the determined concentration to a characteristic of the material of interest by using suitable processing means. As will be appreciated, the optical computing devices may be configured to detect as many characteristics as desired for a given material of interest. All that is required to accomplish the monitoring of multiple characteristics of interest is the incorporation of suitable processing and detection means within the optical computing device for each characteristic of interest (e.g., the concentration of an analyte, the particle size distribution, or the temperature). In some embodiments, the properties of the material of interest can be determined using a combination of characteristics of interest (e.g., a linear, non-linear, logarithmic, and/or exponential combination). Accordingly, the more characteristics that are detected and analyzed using the optical computing devices, the more accurately the properties of the material of interest will be determined. For example, properties of a fluid cement composition that may be determined using optical computing devices described herein may include, but are not limited to, degree of compositional homogeneity, degree of particle size distribution homogeneity, and the like, and any combination thereof.

The optical computing devices described herein utilize electromagnetic radiation to perform calculations, as opposed to the hardwired circuits of conventional electronic processors. When electromagnetic radiation interacts with a material of interest, unique physical and chemical information about the material of interest may be encoded in the electromagnetic radiation that is reflected from, transmitted through, or radiated from the material of interest. This information is often referred to as the spectral "fingerprint" of the material of interest. The optical computing devices described herein are capable of extracting the information of the spectral fingerprint of multiple characteristics of a material of interest (e.g., a dry cement blend, a cement slurry, or an analyte thereof), and converting that information into a detectable output regarding the overall properties of the monitored material of interest. That is, through suitable configurations of the optical computing devices, electromagnetic radiation associated with characteristics of interest in a fluid or analyte thereof can be separated from electromagnetic radiation associated with all other components of the fluid in order to estimate the properties (e.g., density) of the monitored substance (e.g., a cement slurry or other material of interest) in real-time or near real-time.

Figure 1:
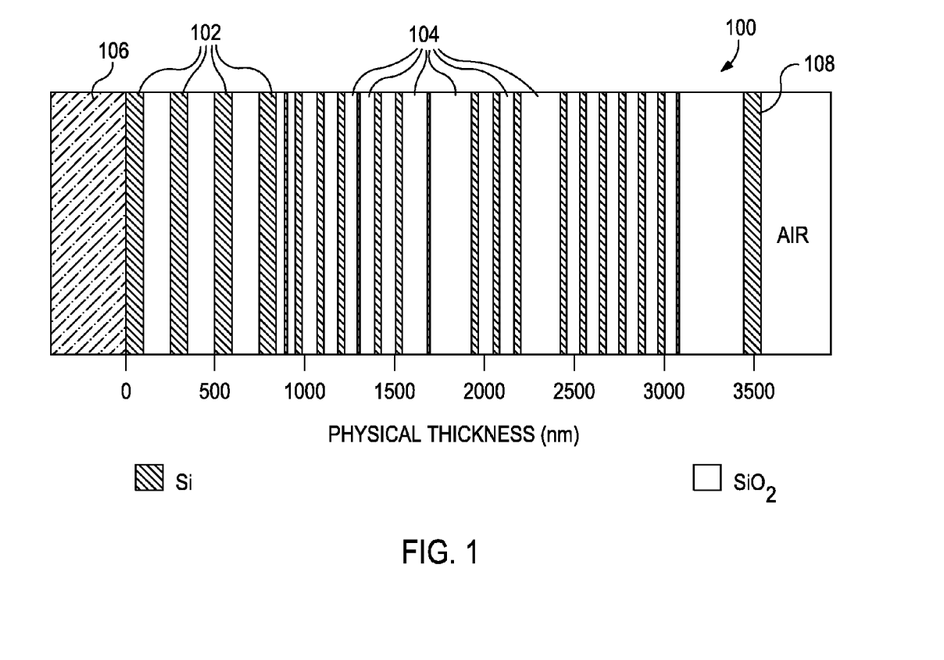
FIG. 1 illustrates an exemplary integrated computation element, according to one or more embodiments.

The processing elements used in the exemplary optical computing devices described herein may be characterized as integrated computational elements (ICE). Each ICE is capable of distinguishing electromagnetic radiation related to the characteristic of interest from electromagnetic radiation related to other components of a fluid. Referring to FIG. 1, illustrated is an exemplary ICE 100 suitable for use in the optical computing devices used in the systems and methods described herein. As illustrated, the ICE 100 may include a plurality of alternating layers 102 and 104, such as silicon (Si) and $SiO_2$ (quartz), respectively. In general, these layers 102, 104 consist of materials whose index of refraction is high and low, respectively. Other examples might include niobia and niobium, germanium and germania, MgF, $SiO_x$, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of interest using a conventional spectroscopic instrument. The spectrum of interest of a given characteristic of interest typically includes any number of different wavelengths. It should be understood that the exemplary ICE 100 in FIG. 1 does not in fact represent any particular characteristic of interest, but is provided for purposes of illustration only. Consequently, the number of layers 102, 104 and their relative thicknesses, as shown in FIG. 1, bear no correlation to any particular characteristic of interest. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and SiO$_2$) may vary, depending on the application, cost of materials, and/or applicability of the materials to the monitored substance.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, digital light pipe (DLP), variable optical attenuators, and/or acousto-optic elements, for example, that can create transmission, reflection, and/or absorptive properties of interest.

The multiple layers 102, 104 exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrograph of the characteristic of interest. These methods may include inverse Fourier transform (IFT) of the optical transmission spectrum and structuring the ICE 100 as the physical representation of the IFT. The approximations convert the IFT into a structure based on known materials with constant refractive indices. Further information regarding the structures and design of exemplary integrated computational elements (also referred to as multivariate optical elements) is provided in *Applied Optics*, Vol. 35, pp. 5484-5492 (1996) and Vol. 129, pp. 2876-2893, which is hereby incorporated by reference.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the output light intensity of the ICE 100 is related to the characteristic of interest. Further details regarding how the exemplary ICE 100 is able to distinguish and process electromagnetic radiation related to the characteristic of interest are described in U.S. Pat. No. 6,198,531 entitled "Optical Computational System;" U.S. Pat. No. 6,529,276 entitled "Optical Computational System;" and U.S. Pat. No. 7,920,258 entitled "Optical Analysis System and Elements to Isolate Spectral Region;" previously incorporated herein by reference.

Figure 2:
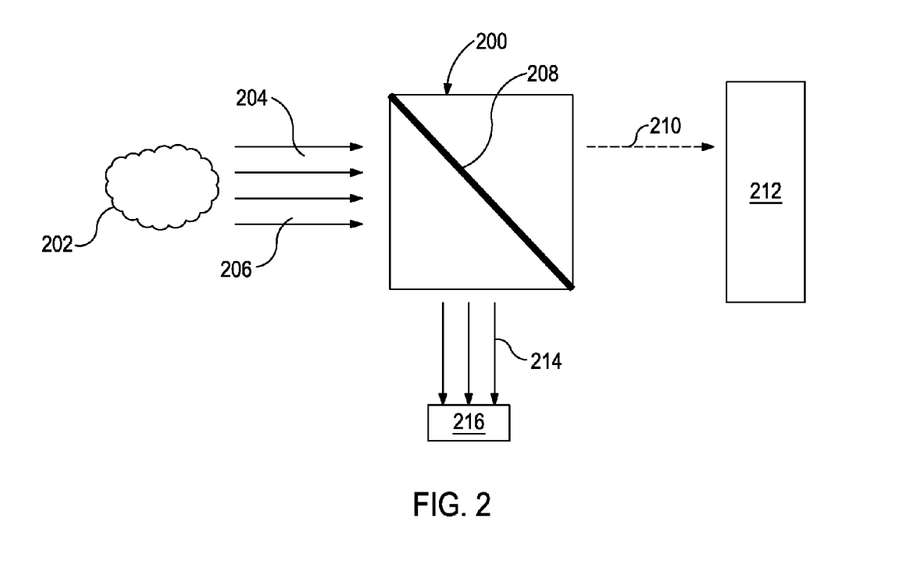
FIG. 2 illustrates a block diagram non-mechanistically illustrating how an optical computing device distinguishes electromagnetic radiation related to a characteristic of interest from other electromagnetic radiation, according to one or more embodiments.

Referring now to FIG. 2, illustrated is a block diagram that non-mechanistically illustrates how an optical computing device 200 is able to distinguish electromagnetic radiation related to a characteristic of interest from other electromagnetic radiation. As shown in FIG. 2, after being illuminated with incident electromagnetic radiation, a fluid 202 (e.g., a dry cement blend or a cement slurry) produces an output of electromagnetic radiation (e.g., sample-interacted light), some of which is electromagnetic radiation 204 corresponding to the characteristic of interest and some of which is background electromagnetic radiation 206 corresponding to other characteristics of the fluid 202. In some embodiments, the fluid 202 may include one or more characteristics of interest that may correspond to the one or more analytes of the fluid 202 (e.g., reagents, products, or other chemical components).

Although not specifically shown, one or more spectral elements may be employed in the device 200 in order to restrict the optical wavelengths and/or bandwidths of the system and thereby eliminate unwanted electromagnetic radiation existing in wavelength regions that have no importance. Such spectral elements can be located anywhere along the optical train, but are typically employed directly after a light source, which provides the initial electromagnetic radiation. Various configurations and applications of spectral elements in optical computing devices may be found in commonly owned U.S. Pat. No. 6,198,531 entitled "Optical Computational System;" U.S. Pat. No. 6,529,276 entitled "Optical Computational System;" U.S. Pat. No. 7,123,844 entitled "Optical Computational System;" U.S. Pat. No. 7,834,999 "Optical Analysis System and Optical Train;" U.S. Pat. No. 7,911,605 entitled "Multivariate Optical Elements for Optical Analysis System;" U.S. Pat. No. 7,920,258 entitled "Optical Analysis System and Elements to Isolate Spectral Region;" and U.S. Pat. No. 8,049,881 entitled "Optical Analysis System and Methods for Operating Multivariate Optical Elements in a Normal Incidence Orientation;" and U.S. patent application Ser. No. 12/094,460 entitled "Methods of High-Speed Monitoring Based on the Use of Multivariate Optical Elements;" Ser. No. 12/094,465 entitled "Optical Analysis System for Dynamic Real-Time Detection and Measurement;" and Ser. No. 13/456,467 entitled "Imaging Systems for Optical Computing Devices;" incorporated herein by reference, as indicated above.

The beams of electromagnetic radiation 204, 206 impinge upon the optical computing device 200, which contains an exemplary ICE 208 therein. In the illustrated embodiment, the ICE 208 may be configured to produce optically interacted light, for example, transmitted optically interacted light 210 and reflected optically interacted light 214. In operation, the ICE 208 may be configured to distinguish the electromagnetic radiation 204 from the background electromagnetic radiation 206.

The transmitted optically interacted light 210, which may be related to the characteristic of interest of the fluid 202, may be conveyed to a detector 212 for analysis and quantification. In some embodiments, the detector 212 is configured to produce an output signal in the form of a voltage that corresponds to the particular characteristic of the fluid 202. In at least one embodiment, the signal produced by the detector 212 and the characteristic of a fluid 202 (e.g., the concentration of an analyte, pH, particle size distribution, or the like) may be directly proportional. In other embodiments, the relationship may be a polynomial function, an exponential function, and/or a logarithmic function. The reflected optically interacted light 214, which may be related to other characteristics of the fluid 202, can be directed away from detector 212. In alternative configurations, the ICE 208 may be configured such that the reflected optically interacted light 214 can be related to the characteristic of interest, and the transmitted optically interacted light 210 can be related to other characteristics in the fluid 202.

In some embodiments, a second detector 216 can be present and arranged to detect the reflected optically interacted light 214. In other embodiments, the second detector 216 may be arranged to detect the electromagnetic radiation 204,206 derived from the fluid 202 or electromagnetic radiation directed toward or before the fluid 202. Without limitation, the second detector 216 may be used to detect radiating deviations stemming from an electromagnetic radiation source (not shown), which provides the electromagnetic radiation (i.e., light) to the device 200. For example, radiating deviations can include such things as, but not limited to, intensity fluctuations in the electromagnetic radiation, interferent fluctuations (e.g., dust or other interferents passing in front of the electromagnetic radiation source), coatings on windows included with the optical computing device 200, combinations thereof, or the like. In some embodiments, a beam splitter (not shown) can be employed to split the electromagnetic radiation 204,206, and the transmitted or reflected electromagnetic radiation can then be directed to two or more ICE 208. That is, in such embodiments, the ICE 208 does not function as a type of beam splitter, as depicted in FIG. 2, and the transmitted or reflected electromagnetic radiation simply passes through the ICE 208, being computationally processed therein, before travelling to the detector 212.

The characteristic(s) of interest being analyzed using the optical computing device 200 can be further processed and/or analyzed computationally to provide additional characterization information about the fluid 202 or an analyte thereof. In some embodiments, the identification and concentration of each analyte of interest in the fluid 202 can be used to predict certain physical characteristics of the fluid 202. For example, the bulk characteristics of the fluid 202 can be estimated by using a combination of the properties conferred to the fluid 202 by each analyte.

In some embodiments, the concentration or magnitude of the characteristic of interest determined using the optical computing device 200 can be fed into an algorithm operating under computer control. The algorithm may be configured to make predictions on how the characteristics of the fluid 202 would change if the concentrations of the characteristic of interest are changed relative to one another. In some embodiments, the algorithm can produce an output that is readable by an operator who can manually take appropriate action, if needed, based upon the reported output. In other embodiments, however, the algorithm can take proactive process control by, for example, automatically adjusting the flow rates of fluids (e.g., fluids flowing through the flow path like in placing a fluid cement composition in a wellbore and/or fluids flowing into a flow path like in preparing a cement slurry) being introduced into a flow path or by halting the introduction of the fluid in response to an out of range condition, for example, if a cement slurry density is out of specification.

In some embodiments, the characteristics of interest determined using the optical computing devices 200 can be associated with a timestamp. A timestamp may be useful in reviewing and analyzing the history of the characteristic of interest, which may be of added value in building a library of cement processes relating to fluid cement compositions, e.g., cement setting processes and/or bulk blending processes where dry cement blends, water, and/or other analytes are metered together and mixed to produce cement slurries. In some embodiments, the characteristics of interest, optionally timestamped, can be fed into an algorithm operating under computer control. The algorithm may be configured to make predictions on the status of the cement processes relating to fluid cement compositions and/or any operational parameters that need to be changed as described further below. In some embodiments, the algorithm can produce an output that is readable by an operator who can manually take appropriate action, like initiation of a remedial operation, if needed, based upon the output.

The algorithm can be part of an artificial neural network configured to use the concentration of each characteristic of interest in order to evaluate the overall characteristic(s) of the fluid 202 and predict how to modify the fluid 202 in order to alter its properties in a desired way. Illustrative but non-limiting artificial neural networks are described in commonly owned U.S. patent application Ser. No. 11/986,763 entitled "Determining Stimulation Design Parameters Using Artificial Neural Networks Optimized with a Genetic Algorithm," which is incorporated herein by reference. It is to be recognized that an artificial neural network can be trained using samples of predetermined characteristics of interest, such as known reagents and products resulting from chemical processes involving such reagents, having known concentrations, compositions, and/or properties, and thereby generating a virtual library. As the virtual library available to the artificial neural network becomes larger, the neural network can become more capable of accurately predicting the characteristic of interest corresponding to a fluid or analyte thereof. Furthermore, with sufficient training, the artificial neural network can more accurately predict the characteristics of the fluid, even in the presence of unknown analytes.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM, and flash EPROM.

In some embodiments, the data collected using the optical computing devices can be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system can also allow remote monitoring and operation of a chemical reaction process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site (e.g., via wireless technology).

Figure 3:
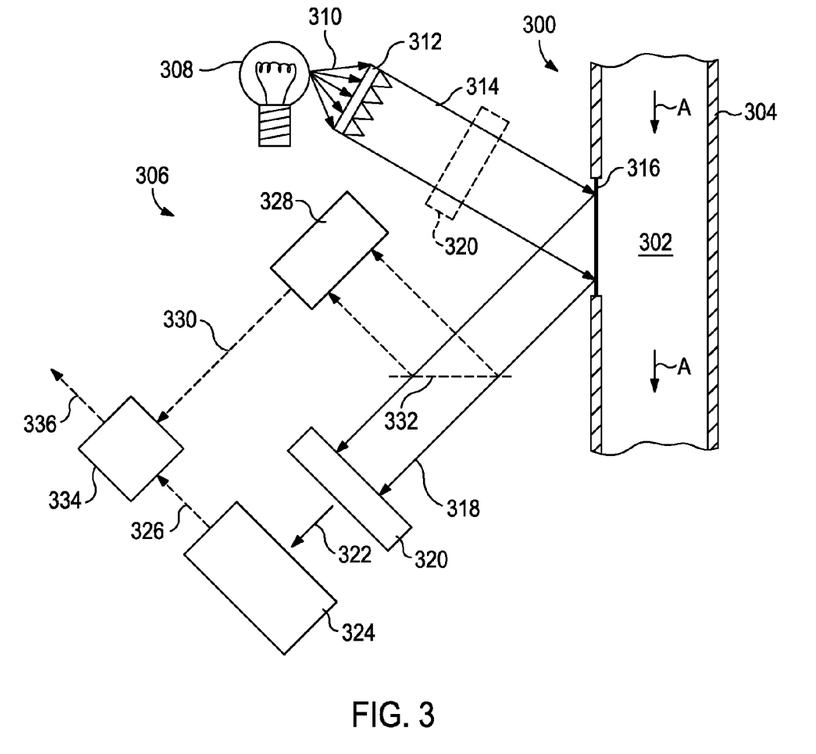
FIG. 3 illustrates an exemplary system for monitoring a fluid present in a flow path, according to one or more embodiments.

Referring now to FIG. 3, illustrated is an exemplary system 300 for monitoring a fluid 302, according to one or more embodiments. In some embodiments, the fluid 302 may be a dry cement blend or a cement slurry, but in other embodiments the fluid 302 may be any fluid as generally defined above. In the illustrated embodiment, the fluid 302 may be contained or otherwise flowing within an exemplary flow path 304. In at least one embodiment, the flow path 304 may be a flow line or a pipeline and the fluid 302 present therein may be flowing in the general direction indicated by the arrows A (i.e., from upstream to downstream). As will be appreciated, however, in other embodiments the flow path 304 may be any other type of flow path, as generally described or otherwise defined herein. For example, the flow path 304 may be a storage or reaction vessel and the fluid 302 may not necessarily be flowing while being monitored.

In at least one embodiment, however, the flow path 304 may form part of a pipeline and may be part of a wellhead or a plurality of subsea and/or above-ground interconnecting flow lines or pipes that interconnect various subterranean hydrocarbon reservoirs with one or more receiving/gathering platforms or process facilities. In some embodiments, portions of the flow path 304 may be employed downhole and fluidly connect, for example, a formation and a wellhead. As such, portions of the flow path 304 may be arranged substantially vertical, substantially horizontal, or any directional configuration therebetween, without departing from the scope of the disclosure. In yet other embodiments, the flow path 304 may be an annulus formed between a subterranean formation and casing string, or the like.

The system 300 may include at least one optical computing device 306, which may be similar in some respects to the optical computing device 200 of FIG. 2, and therefore may be best understood with reference thereto. While not shown, the optical computing device 306 may be housed within a casing or housing configured to substantially protect the internal components of the device 306 from damage or contamination from the external environment (e.g., the flow path 304). The housing may operate to mechanically couple the device 306 to the flow path 304 with, for example, mechanical fasteners, brazing or welding techniques, adhesives, magnets, combinations thereof or the like. In operation, the housing may be designed to withstand the pressures that may be experienced within or outside the flow path 304 and thereby provide a fluid tight seal against external contamination.

As described in greater detail below, the optical computing device 306 may be useful in determining a particular characteristic of the fluid 302 within the flow path 304, such as determining a concentration of an analyte present within the fluid 302 or determining the hydration level of an analyte of the fluid 302 (e.g., the hydration level of a cementitious particle). In some embodiments, the optical computing device 306 may be useful in determining a particular characteristic of the fluid 302 within the flow path 304 at the corresponding location along the flow path 304, which as described in more detail below may be advantageous when two or more optical computing devices 306 are implemented along flow path 304 and/or along multiple flow paths.

Knowing at least some of the characteristics of the fluid 302, e.g., the concentration of analytes, hydration levels, particle size distribution, and the like, may help determine the overall quality of the fluid 302. Further, monitoring at least some of the characteristics of the fluid 302 over time (i.e., over a plurality of time points) with the optical computing device 306 may help determine changes in the quality of the fluid 302. Knowing the quality of the fluid 302, based on a single measurement or measurements at a plurality of time points, provides an opportunity to remedy potentially undesirable parameters of the fluid 302, e.g., by mixing or the addition of analytes, or an indicator that the fluid 302 is ready for implementation. This may prove especially advantageous in a cementing operation. For example, a dry cement blend may, over time, settle, which can be monitored by measuring the particle distribution, either over time or at a single point in time compared to a standard value. If the particle size distribution deviates out of a predetermined specification, mixing can be initiated to effectively redistribute the particles appropriately.

In some embodiments, the device 306 may include an electromagnetic radiation source 308 configured to emit or otherwise generate electromagnetic radiation 310. The electromagnetic radiation source 308 may be any device capable of emitting or generating electromagnetic radiation, as defined herein. For example, the electromagnetic radiation source 308 may be a light bulb, a light emitting device (LED), a laser, a blackbody, a photonic crystal, an X-Ray source, combinations thereof, or the like. In some embodiments, a lens 312 may be configured to collect or otherwise receive the electromagnetic radiation 310 and direct a beam 314 of electromagnetic radiation 310 toward the fluid 302. The lens 312 may be any type of optical device configured to transmit or otherwise convey the electromagnetic radiation 310 as desired. For example, the lens 312 may be a normal lens, a Fresnel lens, a diffractive optical element, a holographic graphical element, a mirror (e.g., a focusing mirror), a type of collimator, or any other electromagnetic radiation transmitting device known to those skilled in art. In other embodiments, the lens 312 may be omitted from the device 306 and the electromagnetic radiation 310 may instead be conveyed toward the fluid 302 directly from the electromagnetic radiation source 308.

In one or more embodiments, the device 306 may also include a sampling window 316 arranged adjacent to or otherwise in contact with the fluid 302 for detection purposes. The sampling window 316 may be made from a variety of transparent, rigid or semi-rigid materials that are configured to allow transmission of the electromagnetic radiation 310 therethrough. For example, the sampling window 316 may be made of, but is not limited to, glasses, plastics, semi-conductors, crystalline materials, polycrystalline materials, hot or cold-pressed powders, combinations thereof, or the like. In order to remove ghosting or other imaging issues resulting from reflectance on the sampling window 316, the system 300 may employ one or more internal reflectance elements (IRE), such as those described in co-owned U.S. Pat. No. 7,697,141 entitled "In Situ Optical Computational Fluid Analysis System and Method," and/or one or more imaging systems, such as those described in co-owned U.S. patent application Ser. No. 13/456,467 entitled "Imaging Systems for Optical Computing Devices," the contents of each hereby being incorporated by reference.

After passing through the sampling window 316, the electromagnetic radiation 310 impinges upon and optically interacts with the fluid 302, including any analytes present within the fluid 302. As a result, optically interacted radiation 318 is generated by and reflected from the fluid 302. Those skilled in the art, however, will readily recognize that alternative variations of the device 306 may allow the optically interacted radiation 318 to be generated by being transmitted, scattered, diffracted, absorbed, emitted, or re-radiated by and/or from the fluid 302, or one or more analytes present within the fluid 302, without departing from the scope of the disclosure.

The optically interacted radiation 318 generated by the interaction with the fluid 302 may be directed to or otherwise received by an ICE 320 arranged within the device 306. The ICE 320 may be a spectral component substantially similar to the ICE 100 described above with reference to FIG. 1. Accordingly, in operation the ICE 320 may be configured to receive the optically interacted radiation 318 and produce modified electromagnetic radiation 322 corresponding to a particular characteristic of interest of the fluid 302. In particular, the modified electromagnetic radiation 322 is electromagnetic radiation that has optically interacted with the ICE 320, whereby an approximate mimicking of the regression vector corresponding to the characteristic of interest is obtained. In some embodiments, the characteristic of interest corresponds to the fluid 302. In other embodiments, the characteristic of interest corresponds to a particular analyte found in the fluid 302.

It should be noted that, while FIG. 3 depicts the ICE 320 as receiving reflected electromagnetic radiation from the fluid 302, the ICE 320 may be arranged at any point along the optical train of the device 306, without departing from the scope of the disclosure. For example, in one or more embodiments, the ICE 320 (as shown in dashed) may be arranged within the optical train prior to the sampling window 316 and equally obtain substantially the same results. In other embodiments, the sampling window 316 may serve a dual purpose as both a transmission window and the ICE 320 (i.e., a spectral component). In yet other embodiments, the ICE 320 may generate the modified electromagnetic radiation 322 through reflection, instead of transmission therethrough.

Moreover, while only one ICE 320 is shown in the device 306, embodiments are contemplated herein which include the use of at least two ICE components in the device 306 configured to cooperatively determine the characteristic of interest in the fluid 302. For example, two or more ICE may be arranged in series or parallel within the device 306 and configured to receive the optically interacted radiation 318 and thereby enhance sensitivities and detector limits of the device 306. In other embodiments, two or more ICE may be arranged on a movable assembly, such as a rotating disc or an oscillating linear array, which moves such that the individual ICE components are able to be exposed to or otherwise optically interact with electromagnetic radiation for a distinct brief period of time. The two or more ICE components in any of these embodiments may be configured to be either associated or disassociated with the characteristic of interest in the fluid 302. In other embodiments, the two or more ICE components may be configured to be positively or negatively correlated with the characteristic of interest. These optional embodiments employing two or more ICE components are further described in co-pending U.S. patent application Ser. No. 13/456,264 entitled "Methods and Devices for Optically Determining a Characteristic of a Substance," Ser. No. 13/456,405 entitled "Methods and Devices for Optically Determining A Characteristic of a Substance," Ser. No. 13/456,302 entitled "Methods and Devices for Optically Determining A Characteristic of a Substance," and Ser. No. 13/456,327 entitled "Methods and Devices for Optically Determining A Characteristic of a Substance," the contents of which are hereby incorporated by reference in their entireties.

In some embodiments, it may be desirable to monitor more than one characteristic of interest at a time using the device 306. In such embodiments, various configurations for multiple ICE components can be used, where each ICE component is configured to detect a particular and/or distinct characteristic of interest corresponding, for example, to the fluid 302 or an analyte in the fluid 302. In some embodiments, the characteristic of interest can be analyzed sequentially using multiple ICE components that are provided a single beam of electromagnetic radiation being reflected from or transmitted through the fluid 302. In some embodiments, as briefly mentioned above, multiple ICE components can be arranged on a rotating disc, where the individual ICE components are only exposed to the beam of electromagnetic radiation for a short time. Advantages of this approach can include the ability to analyze multiple characteristics of interest within the fluid 302 using a single optical computing device and the opportunity to assay additional characteristics simply by adding additional ICE components to the rotating disc corresponding to those additional characteristics.

In other embodiments, multiple optical computing devices can be placed at a single location along the flow path 304, where each optical computing device contains a unique ICE that is configured to detect a particular characteristic of interest. In such embodiments, a beam splitter can divert a portion of the electromagnetic radiation being reflected by, emitted from, or transmitted through the fluid 302 and into each optical computing device. Each optical computing device, in turn, can be coupled to a corresponding detector or detector array that is configured to detect and analyze an output of electromagnetic radiation from the respective optical computing device. Parallel configurations of optical computing devices can be particularly beneficial for applications that require low power inputs and/or no moving parts.

Those skilled in the art will appreciate that any of the foregoing configurations can further be used in combination with a series configuration in any of the present embodiments. For example, two optical computing devices having a rotating disc with a plurality of ICE components arranged thereon can be placed in series for performing an analysis at a single location along the length of the flow path 304. Likewise, multiple detection stations, each containing optical computing devices in parallel, can be placed in series for performing a similar analysis.

The modified electromagnetic radiation 322 generated by the ICE 320 may subsequently be conveyed to a detector 324 for quantification of the signal. The detector 324 may be any device capable of detecting electromagnetic radiation, and may be generally characterized as an optical transducer. In some embodiments, the detector 324 may be, but is not limited to, a thermal detector such as a thermopile or photoacoustic detector, a semiconductor detector, a piezoelectric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 324 may be configured to produce an output signal 326 in real-time or near real-time in the form of a voltage (or current) that corresponds to the particular characteristic of interest in the fluid 302. The voltage returned by the detector 324 is essentially the dot product of the optical interaction of the optically interacted radiation 318 with the respective ICE 320 as a function of the concentration of the characteristic of interest. As such, the output signal 326 produced by the detector 324 and the concentration of the characteristic of interest may be related, for example, directly proportional. In other embodiments, however, the relationship may correspond to a polynomial function, an exponential function, a logarithmic function, and/or a combination thereof.

In some embodiments, the device 306 may include a second detector 328, which may be similar to the first detector 324 in that it may be any device capable of detecting electromagnetic radiation. Similar to the second detector 216 of FIG. 2, the second detector 328 of FIG. 3 may be used to detect radiating deviations stemming from the electromagnetic radiation source 308. Undesirable radiating deviations can occur in the intensity of the electromagnetic radiation 310 due to a wide variety of reasons and potentially causing various negative effects on the output of the device 306. These negative effects can be particularly detrimental for measurements taken over a period of time. In some embodiments, radiating deviations can occur as a result of a build-up of film or material on the sampling window 316 which has the effect of reducing the amount and quality of light ultimately reaching the first detector 324. Without proper compensation, such radiating deviations could result in false readings and the output signal 326 would no longer be primarily or accurately related to the characteristic of interest.

To compensate for these types of undesirable effects, the second detector 328 may be configured to generate a compensating signal 330 generally indicative of the radiating deviations of the electromagnetic radiation source 308, and thereby normalize the output signal 326 generated by the first detector 324. As illustrated, the second detector 328 may be configured to receive a portion of the optically interacted radiation 318 via a beamsplitter 332 in order to detect the radiating deviations. In other embodiments, however, the second detector 328 may be arranged to receive electromagnetic radiation from any portion of the optical train in the device 306 in order to detect the radiating deviations, without departing from the scope of the disclosure.

In some applications, the output signal 326 and the compensating signal 330 may be conveyed to or otherwise received by a signal processor 334 communicably coupled to both the detectors 320,328. The signal processor 334 may be a computer including a non-transitory machine-readable medium, and may be configured to computationally combine the compensating signal 330 with the output signal 326 in order to normalize the output signal 326 in view of any radiating deviations detected by the second detector 328. In some embodiments, computationally combining the output and compensating signals 326,330 may entail computing a ratio of the two signals 326,330. For example, the concentration or magnitude of each characteristic of interest determined using the optical computing device 306 can be fed into an algorithm run by the signal processor 334. The algorithm may be configured to make predictions on how the characteristics of the fluid 302 change if the concentration of the measured characteristic of interest changes.

In real-time or near real-time, the signal processor 334 may be configured to provide a resulting output signal 336 corresponding to the characteristic of interest described herein. In some embodiments, as briefly discussed above, the resulting output signal 336 may be readable by an operator who can consider the results and make proper adjustments to the flow path 304 or take appropriate action, if needed, based upon the magnitude of the measured characteristic of interest. In some embodiments, the resulting output signal 336 may be conveyed, either wired or wirelessly, to the user for consideration.

In some embodiments, the resulting output signal 336 may be recognized by the signal processor 334 as being within or without a predetermined or preprogrammed range of suitable operation. For example, the signal processor 334 may be programmed with a characteristic profile that corresponds to one or more characteristics of the flow path 304, e.g., an analyte concentration, a hydration level, a particle size distribution, and the like. In some embodiments, the concentration of an analyte may be measured in the parts per million range, but in other embodiments, the concentration of an analyte may be measured in the parts per billion or thousand range, each of which may have corresponding characteristic profiles. If the resulting output signal 336 exceeds or otherwise falls within a predetermined or preprogrammed range of operation for the characteristic profile, the signal processor 334 may be configured to alert the user (wired or wirelessly) of the same such that appropriate corrective action may be initiated, if needed. In some embodiments, however, the signal processor 334 may be configured to autonomously undertake the appropriate corrective action. Corrective actions may include, but are not limited to, additional mixing of the fluid 302, the addition of an analyte, and/or increasing the temperature of the fluid 302. It should be noted that corrective actions may be taken that do not directly involve the characteristic of interest that is outside the characteristic profile. For example, if premature setting is indicated or possibly initiated when the temperature of a cement slurry exceeds a characteristic profile, an analyte like a set retarder may be added to the fluid 302 to mitigate premature setting and, in some instances, change the limits of the characteristic profile.

In one or more embodiments, the resulting output signal 336 may be indicative of a change in the properties of the fluid 302, e.g., a reaction occurring therein, a temperature change, incorporation of a gas (e.g., intentional or unintentional foaming), and the like. In operation, the optical computing device 306 may be configured to determine and report the characteristic of interest in near or real-time, thereby ascertaining intentional and/or unintentional changes in the properties of the fluid 302, e.g., the status of a cement setting process or particulate settling. In some embodiments, the characteristic of interest may be determined more than once over a period of time, compiled, and analyzed to predict continued changes in the properties of the fluid 302.

In some embodiments, changes in the properties of the fluid 302 may lead to corrective actions and/or initiation of an operation. For example, in some embodiments, a first reagent, e.g., water, may be added to the fluid 302 to hydrate a second reagent, e.g., cementitious particles, where the output signal 336 corresponds to a characteristic of interest, e.g., water concentration, hydration levels, or temperature, that is indicative of the degree of hydration of the second reagent. In another example, the optical computing device 306 may be configured to measure at a plurality of time points the hydration level of a reagent, e.g., a cementitious particle, and determine when the reagent has become fully saturated (e.g., when the saturation level plateaus), which may lead to the initiation of a cementing operation.

Figure 4:
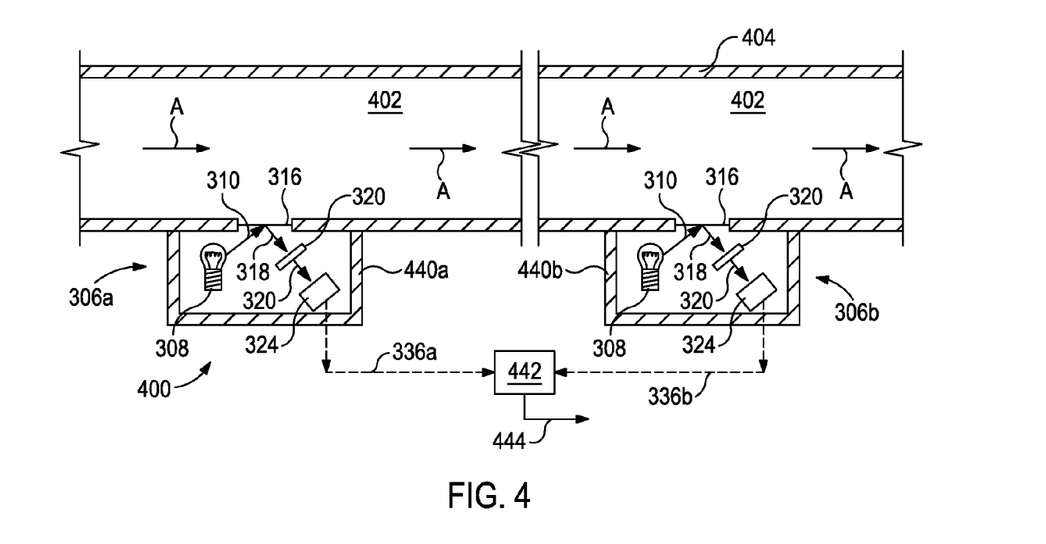
FIG. 4 illustrates an exemplary system for monitoring a fluid present in a flow path, according to one or more embodiments.

Referring now to FIG. 4, with continued reference to FIG. 2 and FIG. 3, illustrated is an exemplary system 400 for monitoring a fluid 402, according to one or more embodiments. In the illustrated embodiment, the fluid 402 may be contained or otherwise flowing within an exemplary flow path 404. The flow path 404 may be a flow line, a pipeline, or an annulus and the fluid 402 present therein may be flowing in the general direction indicated by the arrows A (i.e., from upstream to downstream). As will be appreciated, however, the flow path 404 may be any other type of flow path or combination of flow paths, as generally described or otherwise defined herein, e.g., a storage container fluidly connected to a pipeline that may optionally be fluidly connected to a mixer or transportation container. As such, portions of the flow path 404 may be independently arranged substantially vertical, substantially horizontal, or any directional configuration therebetween, without departing from the scope of the disclosure.

The system 400 may include at least a first optical computing device 306a and a second optical computing device 306b. The optical computing devices 306a,b may be similar in some respects to the optical computing devices 200,300 of FIGS. 2 and 3, respectively, and like numerals indicate like elements that will not be described in detail relative to FIG. 4. As illustrated, the first and second optical computing devices 306a,b may each be associated with the flow path 404 at independent and distinct monitoring locations along the length of the flow path 404. Specifically, the first optical computing device 306a may be located at a first monitoring location along the flow path 404 and the second optical computing device 306b may be located at a second monitoring location along the flow path 404, where the first monitoring location fluidly communicates with the second monitoring location via contiguous portions of the flow path 404. As described in greater detail herein, each optical computing device 306a,b may be useful in determining a particular characteristic of the fluid 402 within the flow path 404, such as determining a characteristic of interest of the fluid 402 at the corresponding location along the flow path 404.

In some embodiments, the second optical computing device 306b is arranged at a predetermined distance from the first optical computing device 306a along the length of the flow path 404. In other embodiments, however, the first optical computing device 306a may be randomly spaced from the second optical computing device 306b, without departing from the scope of the disclosure. For example, the first and second optical computing devices 306a,b may be spaced from each other at two or more random points in a mixer or at two or more random points in a mixing system (e.g., coupled to a mixer container, coupled to a mixing structure like a paddle, and/or couple to an inlet and/or outlet of the mixer container). Moreover, while only two optical computing devices 306a,b are shown in FIG. 4, it will be appreciated that the system 400 may employ more than two optical computing devices within the flow path 404 (or within two or more fluidly communicable flow paths), without departing from the scope of the disclosure. In such embodiments, each additional optical computing device may be spaced from the first and second optical computing devices 306a,b at predetermined or random distances, depending on the application.

In some embodiments, each device 306a,b may be housed within an individual housing coupled or otherwise attached to the flow path 404 at its respective location. As illustrated, for example, the first device 306a may be housed within a first housing 440a and the second device 306b may be housed within a second housing 440b. In some embodiments, the first and second housings 440a,b may be mechanically coupled to the flow path 404 using, for example, mechanical fasteners, brazing or welding techniques, adhesives, magnets, combinations thereof or the like. Each housing 440a,b may be configured to substantially protect the internal components of the respective devices 306a,b from damage or contamination from the external environment. Moreover, each housing 440a,b may be designed so as to withstand the pressures that may be experienced within the flow path 404 and thereby provide a fluid tight seal between the flow path 404 and the respective housing 440a,b.

In some embodiments, the detector 324 in each device 306a,b may be configured to produce an output signal in real-time or near real-time in the form of a voltage (or current) that corresponds to the particular characteristic of interest in the fluid 402. For example, the detector 324 arranged within the first device 306a may generate a first output signal 336a, and the detector 324 arranged within the second device 306b may generate a second output signal 336b. The voltage returned by each detector 324 is essentially the dot product of the optical interaction of the optically interacted radiation 318 with the respective ICE 320 as a function of the concentration of the characteristic of interest of the fluid 402. As such, each output signal 336a,b produced by its corresponding detector 324 the characteristic of interest in the fluid 402 may be related.

The output signal 336a,b from each device 306a,b may be conveyed to or otherwise received by a signal processor 442 communicably coupled to the detectors 324. The signal processor 442 may be a computer including a non-transitory machine-readable medium, and may employ an algorithm configured to calculate or otherwise determine the differences between the two output signals 336a,b. For example, the first output signal 336a may be indicative of a characteristic of interest in the fluid 402 (e.g., the concentration of an analyte, a particle size distribution, and the like) at the location of the first device 306a along the flow path 404, and the second output signal 336b may be indicative of the characteristic of interest in the fluid 402 at the location of the second device 306b along the flow path 404. Accordingly, the signal processor 442 may be configured to determine how the characteristic of interest in the fluid 402 has changed between the first and second monitoring locations along the flow path 404. In some embodiments, the algorithm employed by the signal processor 442 may take into account the distance between the two devices 306a,b. Depending upon the application, the monitoring distances may be short (e.g., meters or even centimeters), or long (e.g., thousands of miles), mainly depending on the application of interest. For those knowledgeable in the art, they will also appreciate that multiple monitors may be employed at a variety of points along the flow path 404.

In real-time or near real-time, the signal processor 442 may be configured to provide a resulting output signal 444 corresponding to the measured difference in the characteristic of interest in the fluid 402 between the first and second monitoring locations along the flow path 404. In some embodiments, the optical computing devices 306a,b may be configured to measure the characteristic at a plurality of time points to create a history at each location and the signal processor 442 may be configured to provide the resulting output signal 444 corresponding to differences in the histories of the characteristic of interest at each location. Differences in the histories of the characteristic of interest at different locations may help determine the overall quality of the fluid 302 and provide an opportunity to remedy potentially undesirable parameters of the fluid 402.

In some embodiments, the resulting output signal 444 may be conveyed, either wired or wirelessly, to a user for consideration. In other embodiments, the resulting output signal 444 may be recognized by the signal processor 442 as being within or without a predetermined or preprogrammed range of suitable operation. If the resulting output signal 444 exceeds the predetermined or preprogrammed range of operation, the signal processor 442 may be configured to alert the user so appropriate corrective action may be taken, or otherwise autonomously undertake the appropriate corrective action such that the resulting output signal 444 returns to a value falling within the predetermined or preprogrammed range of operation.

Figure 5:
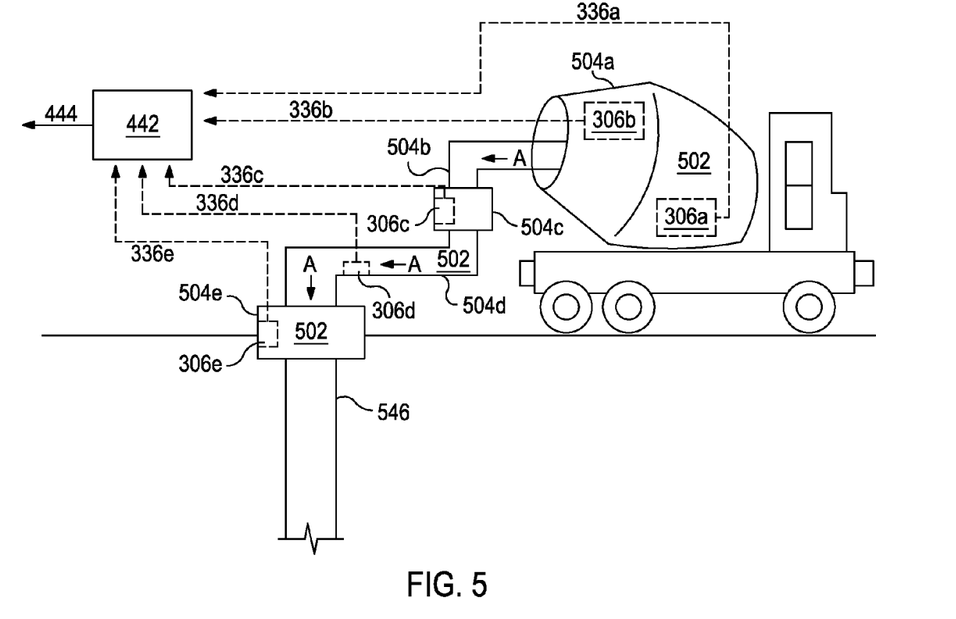
FIG. 5 illustrates an exemplary system for monitoring a fluid present in a flow path, according to one or more embodiments.

Referring now to FIG. 5, with continued reference to FIGS. 2, 3, and 4, illustrated is an exemplary system 500 for monitoring a fluid 502 along flow path 504 (shown as sections 504a, 504b, 504c, 504d, and 504e), according to one or more embodiments.

In the illustrated embodiment, the flow path 504 comprises sections 504a,b,c,d,e, which correspond to a mixer 504a of a truck, a first section of a pipe 504b, a pump 504c, a second section of a pipe 504d, and a wellhead 504e. The fluid 502 present in the flow path 504 may be flowing in the general direction indicated by the arrows A (i.e., from upstream to downstream). As noted above, however, the flow path 504 may be any other type of flow path or combination of flow paths, as generally described or otherwise defined herein, e.g., a storage container fluidly connected to a pipeline that may optionally be fluidly connected to a mixer or transportation container. For example, at least one additional flow path may be included for introduction of analytes into the mixer 504a. Such flow paths may be metered such that changes to the composition of the fluid 502 in the mixer 504a may be changed on-the-fly by an operator and/or a computer algorithm.

A plurality of optical computing devices 306a,b,c,d,e may be disposed along flow path 504 so as to interact with fluid 502 at a desired location. The optical computing devices 306a,b,c,d,e may be similar in some respects to the optical computing devices 200 and 300 of FIGS. 2 and 3, respectively, where like numerals indicate like elements that will not be described again in detail relative to FIG. 5. Further, the handling of signal outputs may be similar in some respects to that described in FIG. 4, and therefore like numerals illustrated in FIG. 4 correspond and will not be described in detail relative to FIG. 5.

The optical computing devices 306a,b,c,d,e each have corresponding output signals 336a,b,c,d,e that can be received and analyzed by the signal processor 442, independently or in any combination of two or more output signals 336a,b,c,d,e. The signal processor 442 can then produce a resulting output signal 444 relating to a characteristic of interest, a comparison of the characteristic of interest at two or more locations, the history of the characteristic of interest, and/or a comparison of the history of the characteristic of interest at two or more locations.

The system 500 may be useful in some embodiments for mixing a dry cement blend with water to yield a cement slurry and introducing the cement slurry into a wellbore 546. In some embodiments, the optical computing devices 306a,b may be useful in determining when the dry cement blend is substantially homogeneous (e.g., by analyzing at a plurality of time points a particle size distribution or analyte concentration during mixing and comparing output signals 336a,b). Once a substantially homogenous dry cement blend is achieved, the water may be added and mixed to yield the cement slurry, where optical computing devices 306a,b may be useful in determining when the cement slurry is ready for introduction into the wellbore 546 (e.g., by analyzing at a plurality of time points for a homogeneous compositional and density levels and comparing respective output signals 336a, b). Depending on the characteristics of interest of the dry cement blend and the cement slurry, optical computing devices 306a,b may be configured to measure more than one characteristic of interest. By measuring at two locations and optionally at a plurality of time points, the analysis for dry cement blend homogeneity and cement slurry homogeneity may be more accurate. Once ready, the cement slurry may be pumped through the flow path 504 with the use of the pump 504c and travel from the mixer 504a through the pipe sections 504b,d and the pump 504c into the wellhead 504e and eventually the wellbore 546.

Systems similar to that illustrated in FIG. 5 may be useful in quality control of cementing operations. For example, if the dry cement blend is not adequately mixed before water introduction, portions of the cement slurry may undergo premature setting while the set time of other portions of the cement slurry may by longer than anticipated. Further, ensuring proper cement-to-water ratio of the cement slurry before introduction into the wellbore may, in some embodiments, ensure the proper set time and/or implementation of set-time retarders or accelerators, which in turn provides for an efficient cementing operation and mitigates cost associated with nonproductive time and mitigation operations, while potentially averting the development of any detrimental outcomes.

Figure 6:
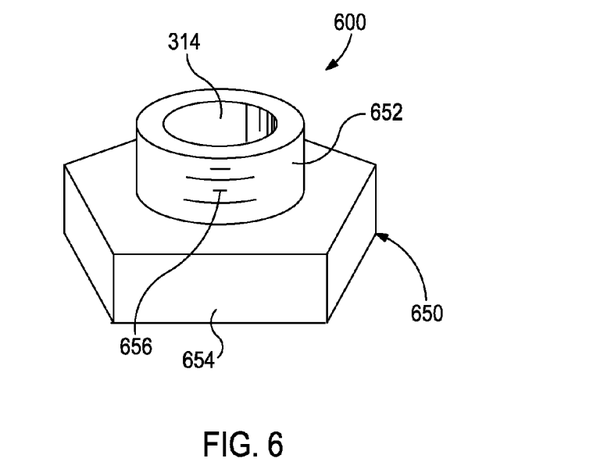
FIG. 6 illustrates an exemplary housing that may be used to house an optical computing device, according to one or more embodiments.

Referring now to FIG. 6, with continued reference to FIGS. 3 and 4, illustrated is an exemplary housing 600 that may be used to house an optical computing device, according to one or more embodiments. The housing 600 may serve the same purpose as the first and second housings 440a and 440b discussed above with reference to FIG. 4 and, in at least one embodiment, may be an alternative embodiment for each housing 440a,b. Those skilled in the art, however, will readily recognize that several alternative designs and configurations of housings used to house the optical computing devices are suitable for the presently disclosed systems and methods. Indeed, the housing embodiments described and disclosed herein are by way of example only, and should not be considered limiting to the exemplary systems and methods disclosed herein.

As illustrated, the housing 600 may be in the general form of a bolt 650 which encloses the various components of an optical computing device, such as one of the first or second optical computing devices 406a,b of FIG. 4. In one embodiment, the components of the optical computing device housed within the housing 600 may be generally housed within a stem 652 of the bolt 650, and the bolt 650 may have a hex head 654 for manual manipulation of the housing 600 using, for example, a wrench or other suitable torque-generating hand tool.

In at least one embodiment, the housing 600 defines external threads 656 that are threadable with corresponding mating pipe threads (not shown) provided in, for example, an opening defined in the flow path 304 (FIG. 3) or 404 (FIG. 4) that is configured to receive the housing 600. The threads 656 may be sealed to the mating pipe threads with a thread sealant in order to help withstand the elevated pressures that may be experienced in the flow path 304, 404. The sampling window 314 is configured to be in optical communication with the fluid 302 (FIG. 3), 402 (FIG. 4) and allows optical interaction between the fluid 302,402 and the other internal components of the internally-housed optical computing device.

Referring again to FIGS. 3 and 4, those skilled in the art will readily recognize that, in one or more embodiments, electromagnetic radiation may be derived from the fluid 302, 402 itself, and otherwise derived independent of the electromagnetic radiation source 308. For example, various substances naturally radiate electromagnetic radiation that is able to optically interact with the ICE 320. In some embodiments, for example, the fluid 302,402 or the substance within the fluid 302,402 may be a blackbody radiating substance configured to radiate heat that may optically interact with the ICE 320. In other embodiments, the fluid 302,402 or the substance within the fluid 302,402 may be radioactive or chemo-luminescent and, therefore, radiate electromagnetic radiation that is able to optically interact with the ICE 320. In yet other embodiments, the electromagnetic radiation may be induced from the fluid 302,402 or the substance within the fluid 302, 402 by being acted upon mechanically, magnetically, electrically, combinations thereof, or the like. For instance, in at least one embodiment, a voltage may be placed across the fluid 302,402 or the substance within the fluid 302,402 in order to induce the electromagnetic radiation. As a result, embodiments are contemplated herein where the electromagnetic radiation source 308 is omitted from the particular optical computing device.

Some embodiments of the present invention may involve optically interacting light from an electromagnetic radiation source with a fluid and at least one integrated computational element, thereby generating optically interacting light, wherein the fluid comprises a cement; receiving with at least one detector the optically interacted light; generating with the at least one detector an output signal corresponding to a characteristic of the fluid; and determining a property of the fluid based on the characteristic of interest. In some embodiments, such a method may occur at more than one location with two or more optical computing devices described herein.

Some embodiments (before, after, and/or during optically interacting the light with the fluid) may further involve mixing the fluid; mixing two or more fluids; introducing at least one analyte described herein into the fluid; increasing the temperature of the fluid; flowing the fluid; transporting the fluid; repeating the steps of optically interacting light, receiving the optically interacted light, and generating the output signal so as to yield a series of output signals corresponding to a history of the characteristic of interest; implementing the fluid in a cementing operation; and any combination thereof.

In some embodiments, the output signal may be correlated to a location corresponding where the fluid was interacted with the light and/or a time corresponding to when the fluid was interacted with the light.

In relation to a dry cement blend, properties of the dry cement blend (e.g., homogeneity, composition, and the like) may be determined using the methods and systems described herein by analyzing, measuring, and/or monitoring at least one characteristic described herein (optionally over time and/or at more than one location), e.g., chemical composition (e.g., identity and concentration in total or of individual analytes), particle size distribution, impurity content, pH, temperature, salt content, opacity, bacteria content, particle size distribution, hydration level, any combination thereof, and the like.

In relation to a cement slurry, properties of the cement slurry (e.g., homogeneity, density, cement setting processes occurring therein, and the like) that may be determined using the methods and systems described herein by analyzing, measuring, and/or monitoring at least one characteristic described herein (optionally over time and/or at more than one location), e.g., chemical composition (e.g., identity and concentration in total or of individual analytes), impurity content, pH, temperature, viscosity, density, ionic strength, total dissolved solids, salt content, opacity, bacteria content, particle size distribution, hydration level, foam quality, any combination thereof, and the like.

In some embodiments, homogeneity of a fluid sample (e.g., dry cement blend, cement slurry, or otherwise) may be achieved by measuring a characteristic of interest at a plurality of time points and analyzing for a plateau in the characteristic of interest (e.g., particle size distribution or chemical composition). In some embodiments, homogeneity of a fluid sample (dry cement blend, cement slurry, or otherwise) may be achieved by measuring a characteristic of interest at two or more locations and analyzing for each characteristic of interest to fall within predetermined limits. In some embodiments, homogeneity of a fluid sample (dry cement blend, cement slurry, or otherwise) may be achieved by a hybrid of the foregoing where analysis involves both comparing the characteristic of interest at various locations and at a plurality of time points.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A method comprising:
   containing within a flow path a dry cement blend;
   optically interacting the dry cement blend with an integrated computational element at a plurality of time points, thereby generating a plurality of output signals corresponding to a characteristic of the dry cement blend at the plurality of time points;
   receiving the plurality of output signals with a signal processor; and
   determining a difference between at least two output signals of the plurality of output signals with the signal processor.

2. The method of claim 1, wherein the difference between the at least two output signals is indicative of how the characteristic of the dry cement blend changes over time.

3. The method of claim 1, wherein the difference between the at least two output signals is indicative of homogeneity of the dry cement blend.

4. The method of claim 1 further comprising:
   mixing the dry cement blend.

5. The method of claim 4 further comprising:
   adding water to the dry cement blend to yield a cement slurry.

6. The method of claim 5 further comprising:
   introducing the cement slurry into a wellbore.

7. The method of claim 1, wherein the characteristic of the dry cement blend is at least one selected from the group consisting of identity of an analyte, concentration of an analyte, pH, temperature, particle size distribution, hydration level, any combination thereof, and the like.

8. The system of claim 7, wherein the analyte is at least one selected from the group consisting of water, salt, a mineral, wollastonite, metakaolin, pumice, a cement, Portland cement, gypsum cement, a calcium phosphate cement, a high alumina content cement, a silica cement, a high alkalinity cement, a fillers, fly ash, fume silica, hydrated lime, pozzolanic material, sand, barite, calcium carbonate, ground marble, iron oxide, manganese oxide, glass bead, crushed glass, a crushed drill cutting, ground vehicle tire, crushed rock, ground asphalt, crushed concrete, crushed cement, ilmenite, hematite, silica flour, fume silica, fly ash, an elastomer, a polymer, diatomaceous earth, a highly swellable clay mineral, nitrogen, air, a fiber, natural rubber, acrylate butadiene rubber, polyacrylate rubber, isoprene rubber, chloroprene rubber, butyl rubber, brominated butyl rubber, chlorinated butyl rubber, chlorinated polyethylene, neoprene rubber, styrene butadiene copolymer rubber, sulphonated polyethylene, ethylene acrylate rubber, epichlorohydrin ethylene oxide copolymer, ethylene propylene rubber, ethylene propylene diene terpolymer rubber, ethylene vinyl acetate copolymer, fluorosilicone rubber, silicone rubber, poly-2,2,1-bicycloheptene, alkylstyrene, crosslinked substituted vinyl acrylate copolymer, nitrile rubber, hydrogenated nitrile rubber, fluoro rubber, perfluoro rubber, tetrafluoroethylene/propylene, starch polyacrylate acid graft copolymer, polyvinyl alcohol cyclic acid anhydride graft copolymer, isobutylene maleic anhydride, acrylic acid type polymer, vinylacetate-acrylate copolymer, polyethylene oxide polymer, carboxymethyl cellulose polymer, starch-polyacrylonitrile graft copolymer, polymethacrylate, polyacrylamide, a non-soluble acrylic polymer, hydrocarbon, an acid, an acid-generating compound, a base, a base-generating compound, a biocide, a surfactant, a scale inhibitor, a corrosion inhibitor, a gelling agent, a crosslinking agent, an anti-sludging agent, a foaming agent, a defoaming agent, an antifoam agent, an emulsifying agent, a de-emulsifying agent, an iron control agent, a proppant or other particulate, a gravel, particulate diverter, a salt, a cement slurry loss control additive, a gas migration control additive, a gas, air, nitrogen, carbon dioxide, hydrogen sulfide, argon, helium, a hydrocarbon gas, methane, ethane, butane, catalyst, a clay control agent, a chelating agent, a corrosion inhibitor, a dispersant, a flocculant, a scavenger, an $H_2S$ scavenger, a $CO_2$ scavenger, an $O_2$ scavenger, a lubricant, a breaker, a delayed release breaker, a friction reducer, a bridging agent, a viscosifier, a weighting agent, a solubilizer, a rheology control agent, a viscosity modifier, a pH control agent, a buffer, a hydrate inhibitor, a relative permeability modifier, a diverting agent, a consolidating agent, a fibrous material, a bactericide, a tracer, a probe, a nanoparticle, a paraffin wax, an asphaltene, a foam, sand, and any combination thereof.

9. A method comprising:
   containing within a flow path a fluid that comprises a cement particle, the flow path providing at least a first monitoring location and a second monitoring location;
   optically interacting the fluid at the first monitoring location with a first integrated computational element, thereby generating a first output signal corresponding to a characteristic of the fluid;
   optically interacting the fluid at the second monitoring location with a second integrated computational element, thereby generating a second output signal corresponding to the characteristic of the fluid;
   receiving the first output signal and the second output signal with a signal processor; and
   determining a difference between the first output signal and the second output signal with the signal processor.

10. The method of claim 9, wherein the fluid is a cement fluid composition.

11. The method of claim 9, wherein the first monitoring location is outside a wellbore and the second monitoring location is within a wellbore.

12. The method of claim 9, wherein the first monitoring location and the second monitoring location are within a wellbore.

13. The method of claim 9, wherein the fluid is a dry cement blend, and the difference between the first output signal and the second output signal is indicative of homogeneity of the dry cement blend.

14. The method of claim 13 further comprising:
adding water to the dry cement blend to yield a cement slurry.

15. The method of claim 14 further comprising:
optically interacting the cement slurry at the first monitoring location with the first integrated computational element, thereby generating a third output signal corresponding to the characteristic of the fluid;
optically interacting the cement slurry at the second monitoring location with the second integrated computational element, thereby generating a fourth output signal corresponding to the characteristic of the fluid;
receiving the first output signal and the second output signal with a signal processor; and
determining a difference between the first output signal and the second output signal with the signal processor.

16. The method of claim 15, wherein the characteristic of the fluid is at least one selected from the group consisting of concentration of an analyte of the fluid, concentration of the cement particle, impurity content, pH, temperature, salt content, opacity, bacteria content, particle size distribution, and hydration level.

17. The method of claim 15 further comprising:
introducing the cement slurry into a wellbore.

18. The method of claim 9, wherein the fluid is a cement slurry; the characteristic of the fluid is at least one selected from the group consisting of concentration of an analyte of the cement slurry, impurity content, pH, temperature, viscosity, density, ionic strength, total dissolved solids, salt content, opacity, bacteria content, particle size distribution, hydration level, and foam quality; and the difference between the first output signal and the second output signal is indicative of homogeneity of the cement slurry.

19. A system comprising:
a flow path containing a dry cement blend; and
at least two optical computing devices arranged in the flow path for monitoring the dry cement blend, each of the at least two optical computing devices independently having at least one integrated computational element configured to optically interact with the dry cement blend and thereby generate optically interacted light, and at least one detector arranged to receive the optically interacted light and generate an output signal corresponding to a characteristic of the dry cement blend.

20. The system of claim 19, wherein the flow path comprises at least one selected from the group consisting of a slurry tank, a flowline, a pipeline, a conduit, a hose, a mixer, a pump, a process facility, a storage vessel, a tanker, a railway tank car, a transport barge or ship, a separator, a contactor, a process vessel, any hybrid thereof, and any combination thereof.

* * * * *